United States Patent [19]
Moriya et al.

[11] Patent Number: 5,428,655
[45] Date of Patent: Jun. 27, 1995

[54] METHOD AND APPARATUS FOR THREE-DIMENSIONAL DETECTION OF PARTICLES

[75] Inventors: Kazuo Moriya, Ageo; Masaru Ohtsuka, Kawagoe, both of Japan

[73] Assignee: Mitsui Mining & Smelting Co., Ltd., Tokyo, Japan

[21] Appl. No.: 119,768

[22] Filed: Sep. 10, 1993

[30] Foreign Application Priority Data

Sep. 14, 1992 [JP] Japan .................. 4-271031

[51] Int. Cl.⁶ .................. G01N 23/00; G01N 23/20; G01N 15/00
[52] U.S. Cl. .................. 378/4; 378/901; 364/413.15; 364/413.16; 364/507; 364/555
[58] Field of Search .................. 364/413.13, 413.14, 364/413.15, 413.16, 481, 567, 555; 378/4, 6, 401

[56] References Cited

U.S. PATENT DOCUMENTS

| | | | |
|---|---|---|---|
| 4,548,500 | 10/1985 | Wyatt et al. | 356/336 |
| 4,769,776 | 9/1988 | Hiraoka et al. | 364/555 |
| 4,884,225 | 11/1989 | Fogarty et al. | 364/559 |
| 4,922,421 | 5/1990 | Tam | 364/413.25 |
| 5,365,429 | 11/1994 | Carmen | 364/413.13 |

*Primary Examiner*—Paul M. Dzierzynski
*Assistant Examiner*—David Vernon Bruce
*Attorney, Agent, or Firm*—Bucknam and Archer

[57] ABSTRACT

The position, size, structure, and the like of each particle can be accurately detected. Gray image data of a tomographic image group having a clear positional correlation in a sample where particles are distributed is obtained to obtain three-dimensional gray image data of each particle. Binarization of a density of each pixel data of the three-dimensional gray image data is performed to obtain three-dimensional binary image data of each particle. Three-dimensional shrinkage of the three-dimensional binary image data is performed to convert binary image data of each particle to binary image data of only a central point thereof, thereby the position of each particle is three-dimensionally confirmed.

15 Claims, 12 Drawing Sheets

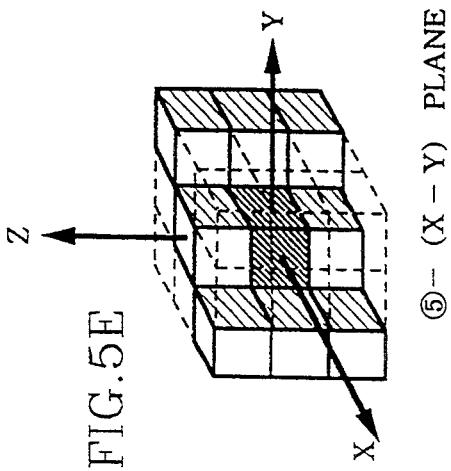
FIG.5E  ⑤—(X−Y) PLANE
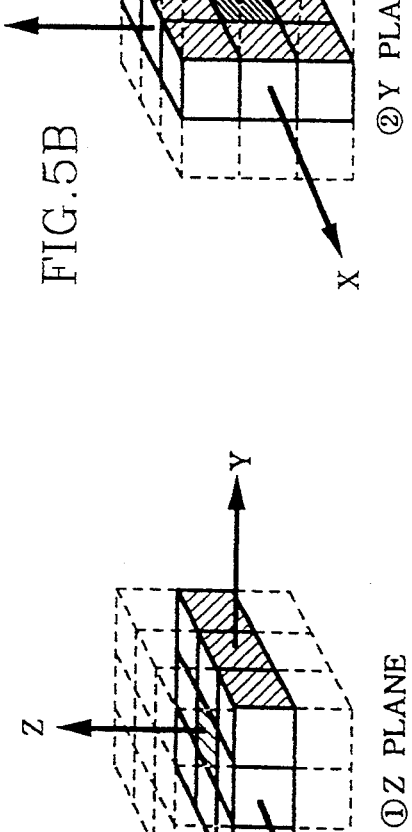
FIG.5B  ②Y PLANE
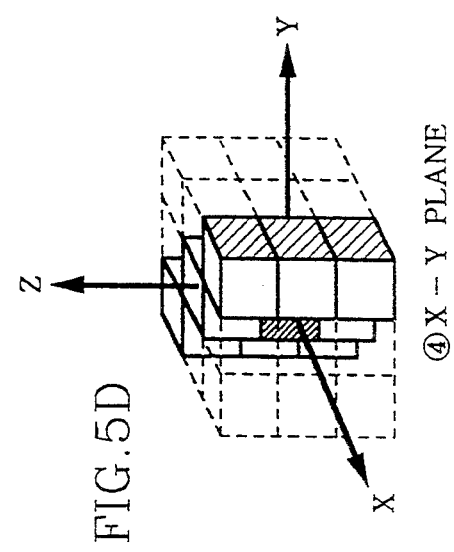
FIG.5D  ④X−Y PLANE
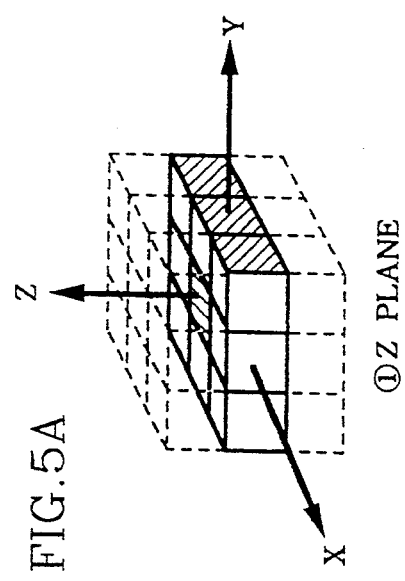
FIG.5A  ①Z PLANE
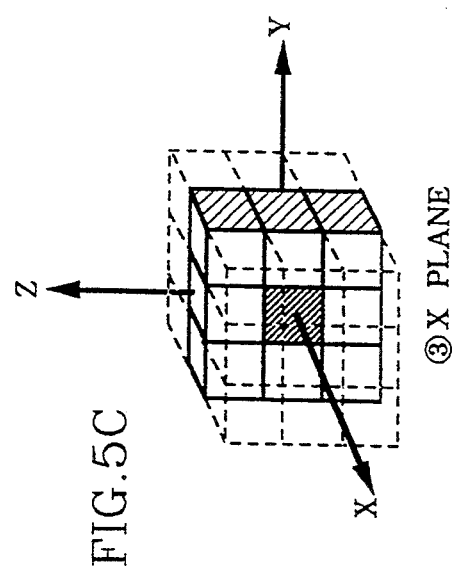
FIG.5C  ③X PLANE

FIG.6A

TABLE 1

FIG.6B

TABLE 2

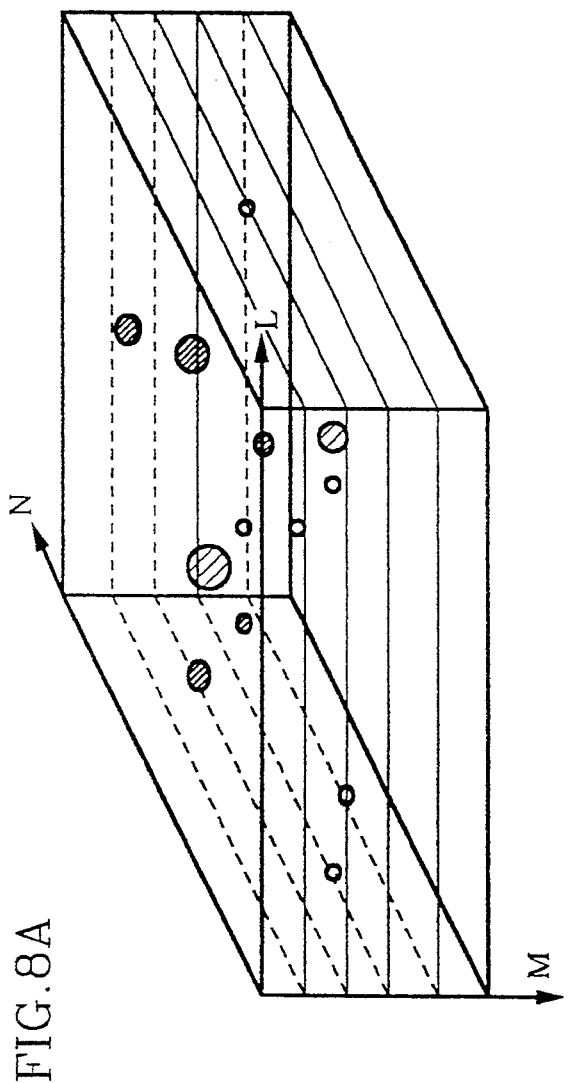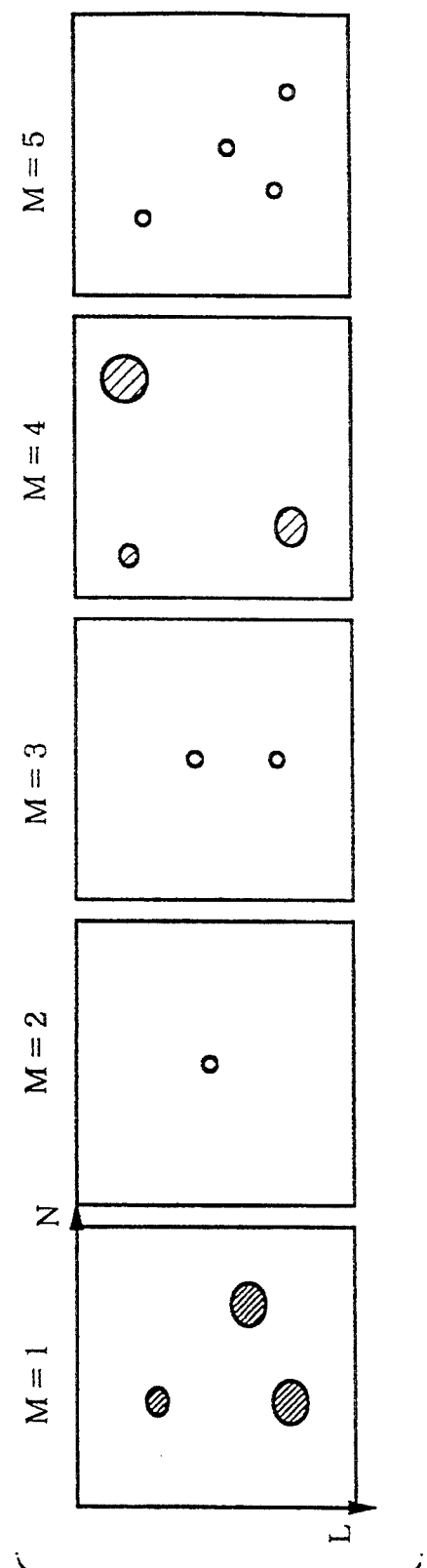
FIG.8A
FIG.8B

PRIOR ART

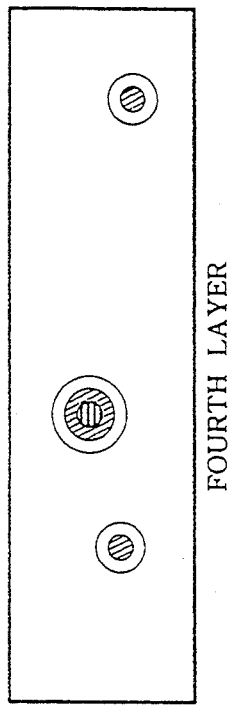
FIG.12D FOURTH LAYER
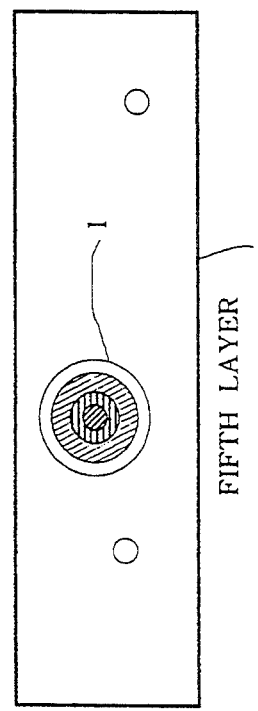
FIG.12E FIFTH LAYER
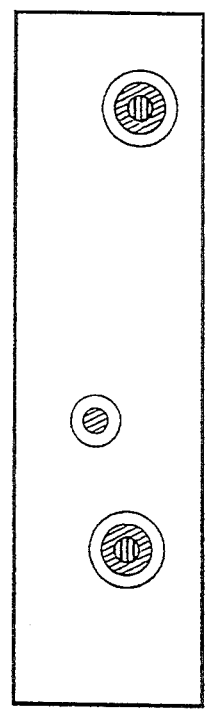
FIG.12F SYNTHESIS OF ALL LAYERS
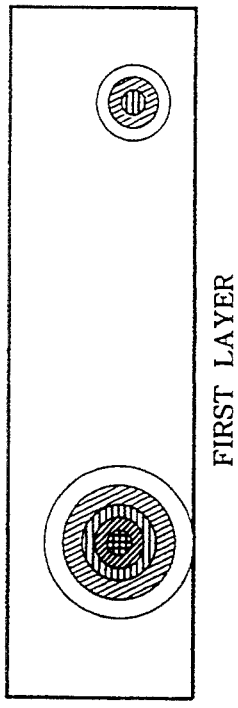
FIG.12A FIRST LAYER
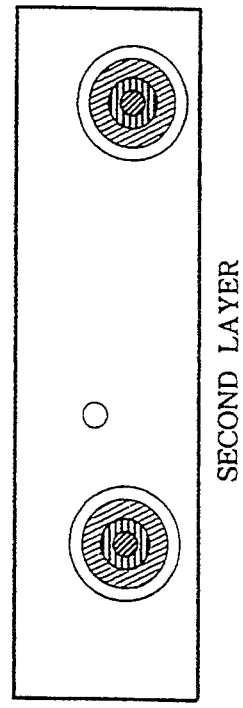
FIG.12B SECOND LAYER
FIG.12C THIRD LAYER

METHOD AND APPARATUS FOR THREE-DIMENSIONAL DETECTION OF PARTICLES

BACKGROUND OF THE INVENTION

1. Field of the Invention

The present invention relates to a method and apparatus for accurately detecting the position, density, and the like of each particle distributed in a three-dimensional sample.

2. Description of the Prior Art

Many conventional image processing techniques process two-dimensional images due to structures of image processing equipments. This is because conventional image processing equipments can process two-dimensional information but cannot directly process three-dimensional information.

FIG. 10 shows a conventional particle analysis method. Two-dimensional gray image data of three-dimensionally distributed particles 1 is obtained. In an image processing equipment, gray image data has unit data representing a unit image (pixel) 3 called a pixel. Each data has tone information. Referring to FIG. 10, reference numeral 5 denotes a pixel image representing an image of one particle using unit data. It is determined whether each pixel data serves as a peak density point with respect to neighboring data. If so, this pixel data is set to "1"; otherwise, it is set to "0", thereby obtaining a particle image using 1 or 0, i.e., binary image data. Reference numeral 7 denotes a pixel image of one particle using this binary image data. When this pixel image is shrinked, the position of each particle is obtained (Japanese Patent Application No. Hei 4-71593). Reference numeral 9 denotes a shrinked pixel image of one particle.

On the other hand, a method of obtaining a stereoscopic image from a two-dimensional tomographic image group is known as three-dimensional image processing (Japanese Patent Application No. Sho 60-155109). A method of reconstructing a two-dimensional image group obtained by viewing a two-dimensional image group from different directions is a well-known method in X-ray CT or the like.

As a method of obtaining a two-dimensional tomographic image, a light scattering method for causing a laser beam to be incident in a crystal to observe scattered light is known (Japanese Patent Application No. Sho 54-109488). In addition, a "Method and Apparatus for Measuring Particle Distribution" for analyzing an image of this scattered light and obtaining the density distribution of particles contained in a sample is known (Japanese Patent Application No. Sho 63-49848).

A dust counter (laser scattering method) for causing a laser beam to be incident on a dust or the like and counting down pulses of light scattered by the dust or the like is conventionally known for detection of dust and air bubbles in a liquid or air. A method of obtaining a grain size distribution using angular dispersion of light scattering caused by particles is also known.

As shown in FIG. 11, however, when slices 11 are scanned with a laser beam to sequentially observe tomographic images of a crystal or fluid in which particles are contained, the same particle 1 is observed in different sizes on different slices 11. A particle image on each slice is obtained as gray image data. In such a tomographic image group, if a plurality of particles are present, the plurality of particles overlap each other to fail to recognize the number of particles and their sizes in a conventional two-dimensional image processing method.

In the dust counter described above, a laser beam portion for radiating a given particle may not be a peak intensity portion but a tail intensity portion, so that the given particle is detected by this tail portion. In this case, the size of the particle is measured to be smaller than the actual size. To avoid this, scattering images must be obtained with shifts of the laser beam. However, of all the scattering images obtained by shifting the laser beam, a scattering image having a highest level of scattering from the given particle cannot be automatically selected.

SUMMARY OF THE INVENTION

The present invention has been made in consideration of the conventional problems described above, and has its object to provide a method and apparatus for, first, accurately detecting the number of particles in a sample, second, accurately detecting the position of each particle in the sample, and third, accurately detecting the size of each particle.

In order to achieve the above object of the present invention, gray image data of a tomographic image group having a clear positional correlation is obtained to obtain three-dimensional gray image data of each particle, the density of each pixel data of the three-dimensional gray image data is binarized to obtain a three-dimensional binary image data of each particle, and this binary image data is three-dimensionally shrinked to convert the binary image data of each particle into binary data of its central point, thereby three-dimensionally confirming the position of each particle.

In addition, the number of particles contained in a predetermined region is counted on the basis of the degenerated binary image data to detect the density of the particles. Alternatively, the size of each particle at the position represented by the shrinked binary image data is detected on the basis of the density of the gray image data of the tomographic image group. In addition, the gray image data of the tomographic image group in a desired direction is reconstructed on the basis of the shrinked binary image data and the gray image data of the tomographic image group.

For example, the gray image data is obtained such that each slice is scanned with a laser beam, and light scattered from each slice is focused and photoelectrically converted.

In this arrangement, since the gray image data of the tomographic image group is binarized and three-dimensionally shrinked, particles can be independently separated to accurately grasp the position, size, and structure of each particle even if a plurality of particles overlap each other in a direction perpendicular to the slice or a plurality of particles are present within a laser beam diameter.

If a sample is a crystal such as a semiconductor, a particle such as a precipitate inside the crystal influences the physical properties of the crystal such as hardness. To obtain necessary physical properties, the grain size and the structure of the precipitate, and the density thereof must be controlled. This precipitate varies depending on the growth condition of a crystal and a subsequent heat-treated state. According to the present invention, the position, size, structure, and the like of this particle can be accurately detected. The detection results can be effectively used to determine the growth condition of the crystal and the heat-treatment condition and can thus be utilized to obtain a semiconductor crystal having desired physical properties. In addition, according to the present invention, the behaviors of individual particles between images, which are unknown in the tomographic picture group, can be known.

BRIEF DESCRIPTION OF THE DRAWINGS

FIG. 5 is a view for explaining a three-dimensional Rao algorithm executed in the apparatus of FIG. 1;

FIG. 6 shows tables representing data used in the three-dimensional Rao algorithm executed in the apparatus of FIG. 1;

FIG. 8 is a view for explaining a state in which gray image data of a tomographic image group in a desired coordinate system L-M-N in the apparatus of FIG. 1 are reconstructed;

FIG. 12 is a view for explaining a state in which the same particle is observed in different sizes on different slices when tomographic images are sequentially observed according to the conventional method of analyzing the particle.

DETAILED DESCRIPTION OF THE PREFERRED EMBODIMENT

Figure 1:
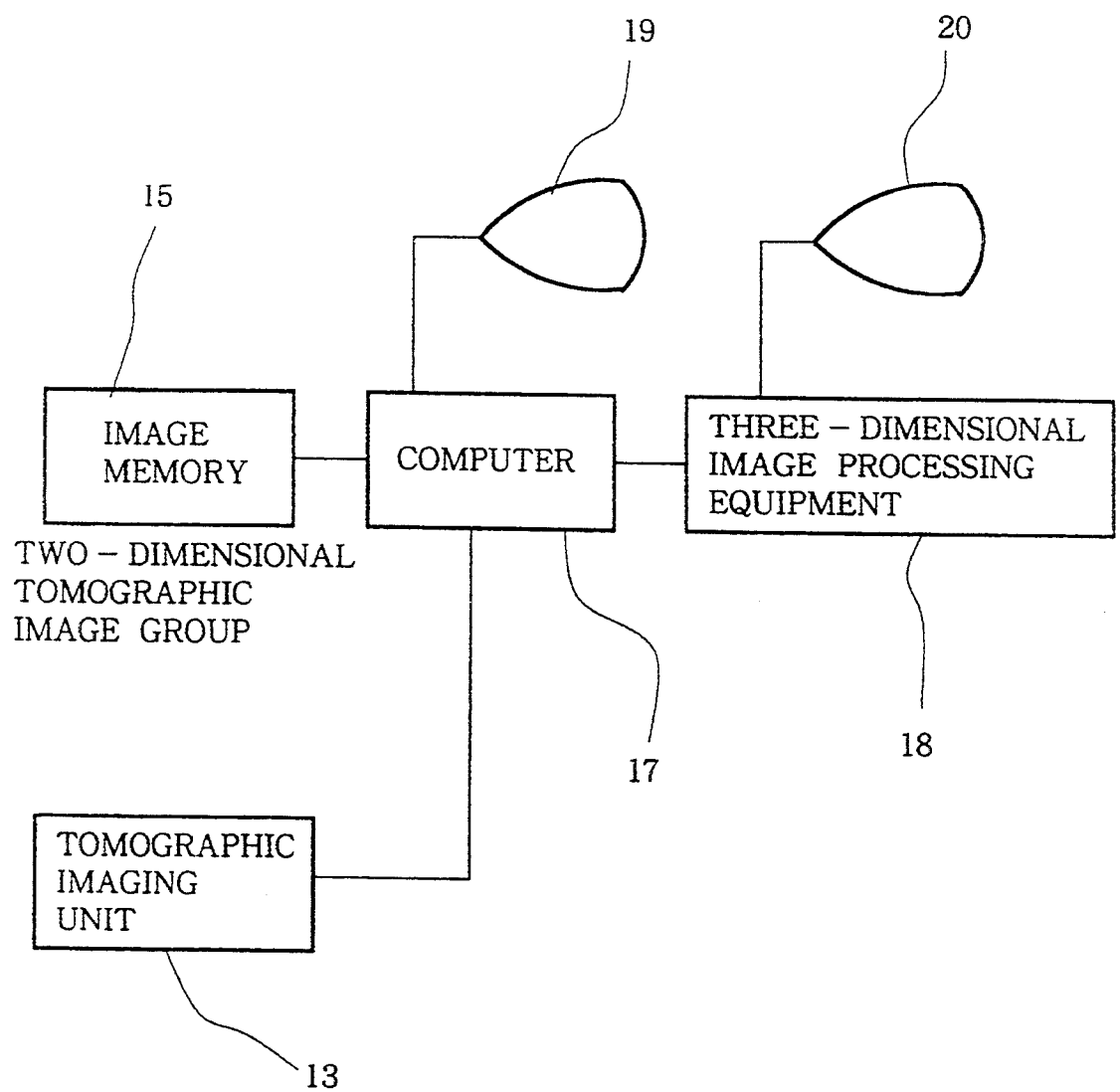
FIG. 1 is a block diagram showing the arrangement of a three-dimensional particle detection apparatus according to an embodiment of the present invention.

FIG. 1 is a block diagram showing the arrangement of a three-dimensional particle detection apparatus according to an embodiment of the present invention. Reference numeral 13 denotes a tomographic imaging unit for obtaining gray image data of a tomographic image group having a clear positional correlation in a sample in which particles are distributed. The tomographic imaging unit comprises, e.g., a means for illuminating each slice of the sample, a means for focusing scattered light and photoelectrically converting it, and a means for converting the photoelectrically converted signal into digital data to obtain gray image data. In addition, the tomographic imaging unit 13 may be a unit for converting two-dimensional tomographic picture groups obtained by various methods into gray image data. Reference numeral 15 denotes a two-dimensional image memory for storing gray image data of the tomographic image group obtained by the tomographic imaging unit 13. Reference numeral 17 denotes a computer; and 19, a CRT. Image data in the two-dimensional image memory is loaded in the computer 17, subjected to predetermined processing, and displayed on the CRT 19.

Reference numeral 18 denotes a three-dimensional image processing equipment for developing the gray image data of the tomographic image group sent from the two-dimensional memory 15 through the computer 17, binarizing the density of each pixel data to obtain three-dimensional binary image data, three-dimensionally performing shrinkage of this binary image data to convert the binary image data of each particle into binary image data of the central point thereof, thereby three-dimensionally confirming the position of each particle. Reference numeral 20 denotes a graphic monitor for displaying a processing result. The processing result of the three-dimensional image processing equipment 18 may be displayed on the CRT 19 through the computer 17.

Figure 2:
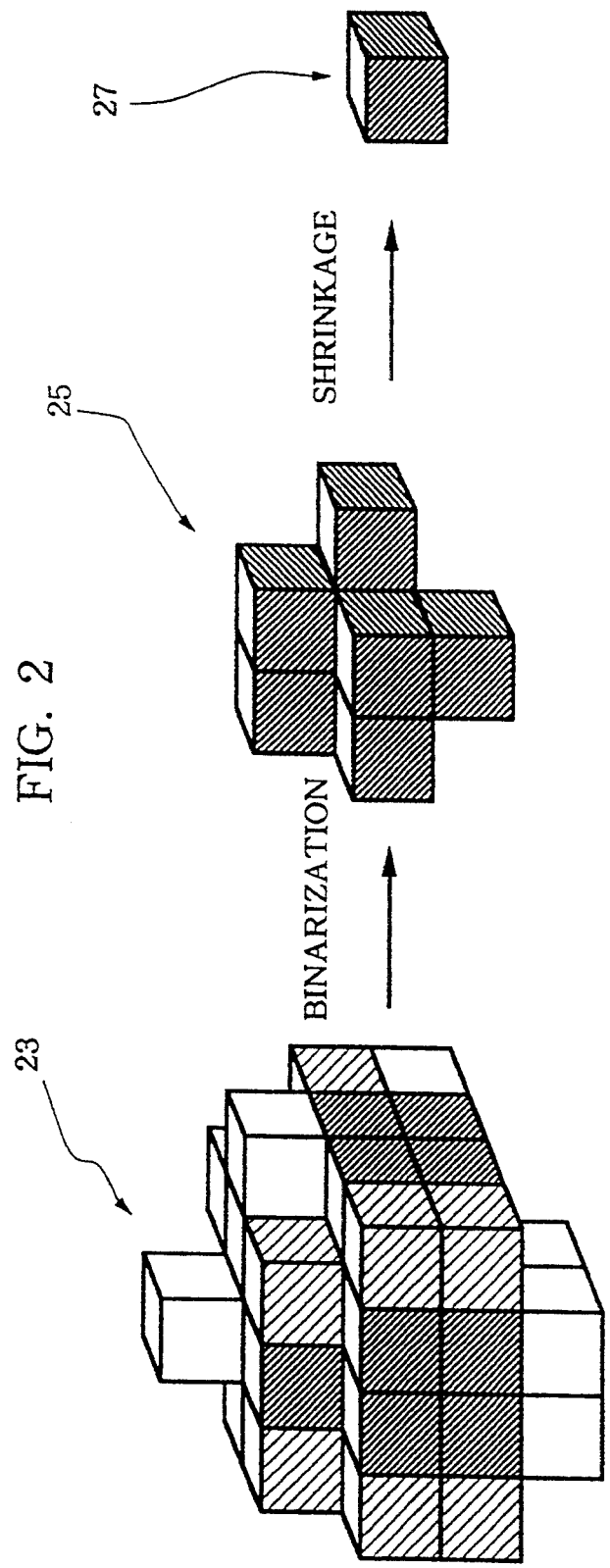
FIG. 2 is a view for explaining confirmation of a position of a particle upon binarization and shrinkage in the apparatus shown in FIG. 1.

With the above arrangement, an original image (two-dimensional image group) stored in the two-dimensional image memory 15 is developed into three-dimensional image data, and this three-dimensional image data is subjected to binarization and shrinkage to obtain the center of the particle, thereby confirming the position of the particle. This state is shown in FIG. 2. To develop the original image into a three-dimensional image is, for example, to add a dimension corresponding to a Z-coordinate to each two-dimensional image group on the X-Y coordinate system and to allow three-dimensional access of each data.

Referring to FIG. 2, reference numeral 23 denotes a one-particle image developed into a three-dimensional image; 25, a binary image thereof; and 27, a binary image representing only the center upon shrinkage. The binarization and shrinkage algorithm for obtaining the center of the particle is an algorithm obtained by expanding a two-dimensional version. The densities near each pixel are three-dimensionally compared with each other in 26 directions. According to this method, three-dimensional shrinkage is performed to achieve convergence to one point, whereas, by the normal two-dimensional binarization and shrinkage, several clusters (pixels) are left to disable convergence to one point. A two-dimensional Rao algorithm is applied to this three-dimensional algorithm.

Figure 3:
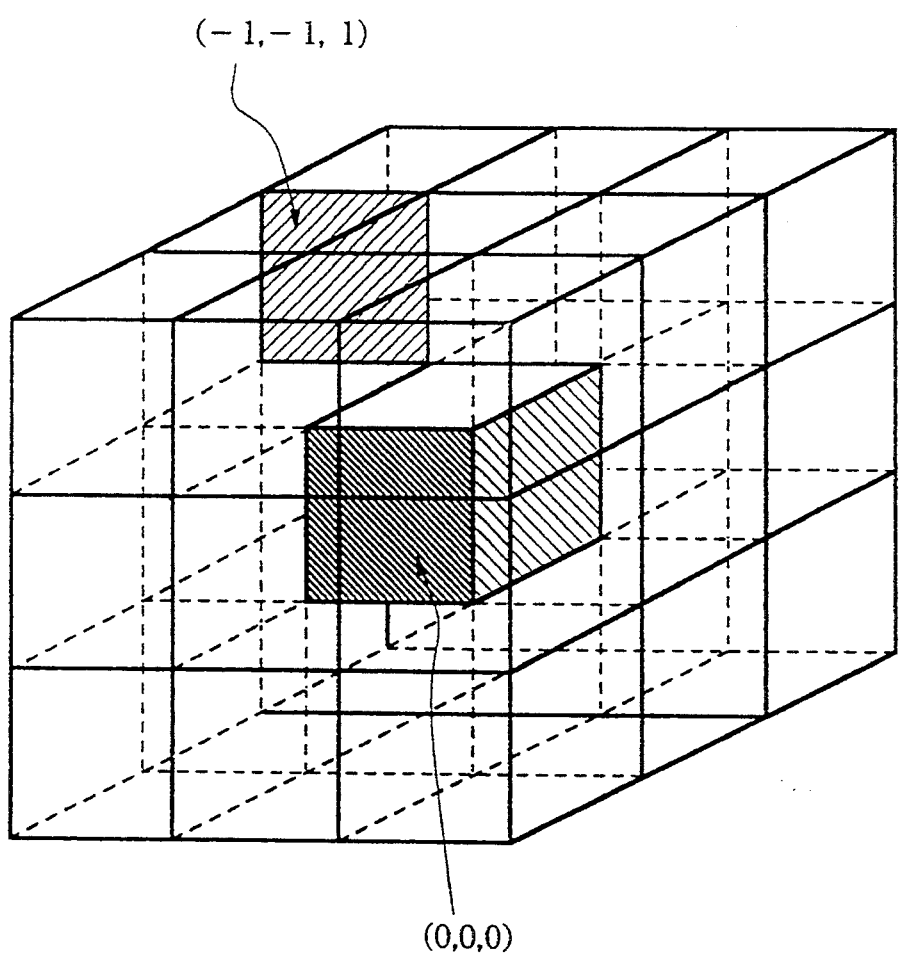
FIG. 3 is a view for explaining a state in which each central candidate point is binarized in the apparatus of FIG. 1.
Figure 4:
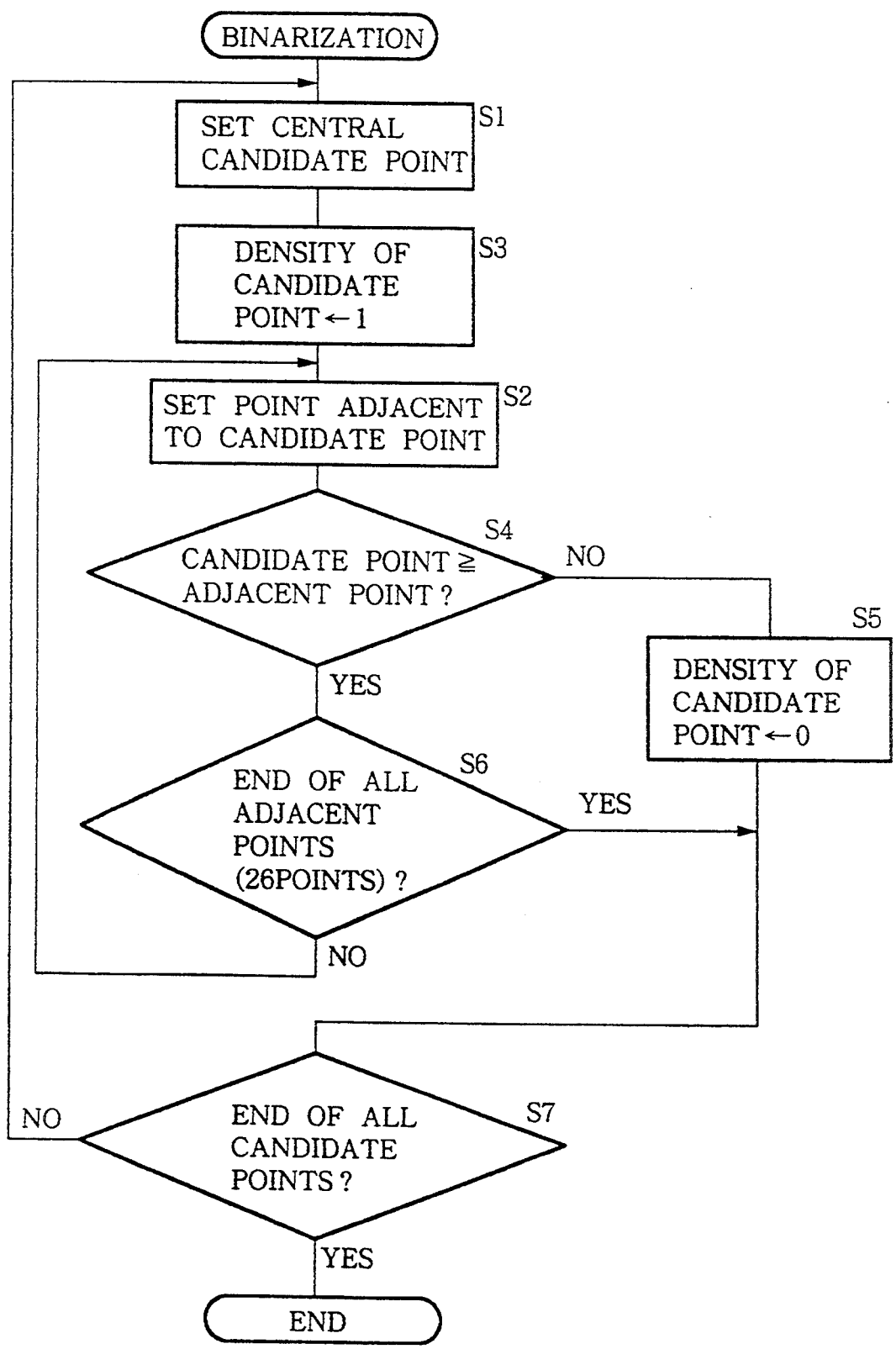
FIG. 4 is a flow chart showing binarization in the apparatus of FIG. 1.

More specifically, data of each pixel of each particle is binarized. As shown in FIG. 3, this binarization is performed such that data (0,0,0) of each central candidate point is compared with data of points adjacent to the central candidate point in 26 directions (3×3×3) if the data of each pixel is the data of the central candidate point. That is, as shown in FIG. 4, a given central candidate point (0,0,0) is set (step S1), and the density of this candidate point is compared with that of data (−1,−1, 1) of one point adjacent to this candidate point (steps S2 and S4). As a result, if the data of the central candidate point (0,0,0) is larger than that of the point adjacent thereto, the density of the candidate point is set to "1", and the flow advances to step S5 (steps S3 and S4); otherwise, the density of the central candidate point is set to "0" (steps S4 and S5), and the flow advances to step S7. It is determined in step S6 whether the central candidate point is compared with all points adjacent thereto. If YES in step S6, the flow advances to step S7; otherwise, the flow returns to step S2. The next adjacent point is set, and the above operations are repeated. It is determined in step S7 whether all the central candidate points are binarized. If NO in step S7, the flow returns to step S1 to set the next central candidate point. However, if YES in step S7, binarization is ended. Therefore, the gray image 23 of each particle is converted into the three-dimensional binary image 25.

The resultant binary image is then subjected to three-dimensional shrinkage. As shown in FIG. 5, the two-dimensional Rao algorithm (e.g., "Introduction to Computer-Aided Image Processing", Hideyuki Tamura, Soken Shuppan) is applied to each central candidate point constituting the binary image on each plane including this central candidate point. A total of 13 planes, i.e., three planes (X, Y, and Z planes), six diagonal planes (e.g., X-Y and X-Z planes), and four oblique planes (e.g., an X-Y-Z plane) must be taken into consideration. If planes in five directions, as shown in FIG. 5, are taken into consideration in place of all the thirteen planes, the central candidate points of each particle can be converged to one point.

Figures 6A, 6B:
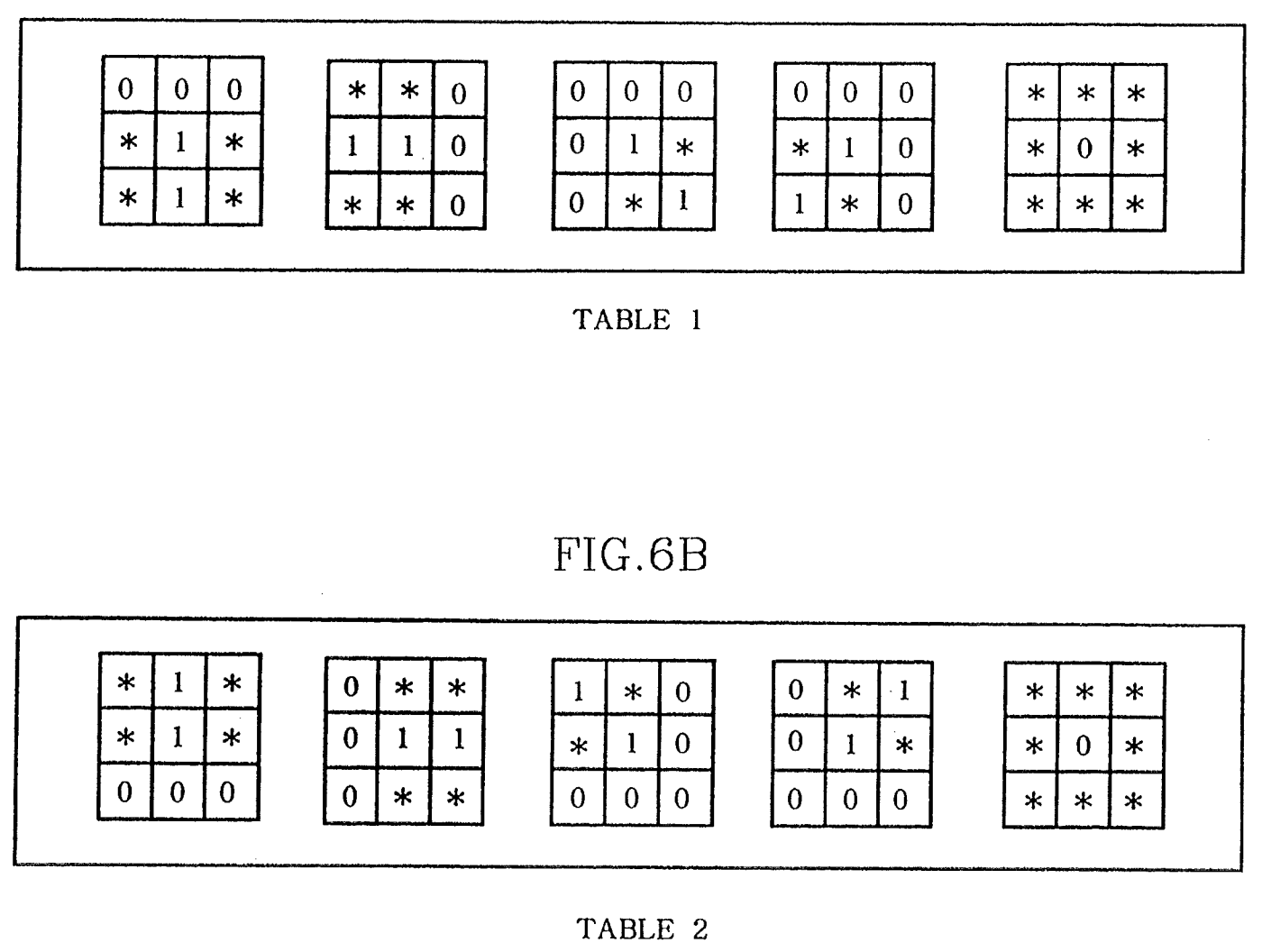

A given particle is taken as an example to explain shrinkage in detail. Using data shown in Tables 1 and 2 in FIG. 6, the Rao algorithm is applied to each plane shown in FIG. 5. Symbol * in Tables 1 and 2 indicates an indeterminate state which can be "1" or "0" state (this state is not subjected to comparison).

Figure 7:
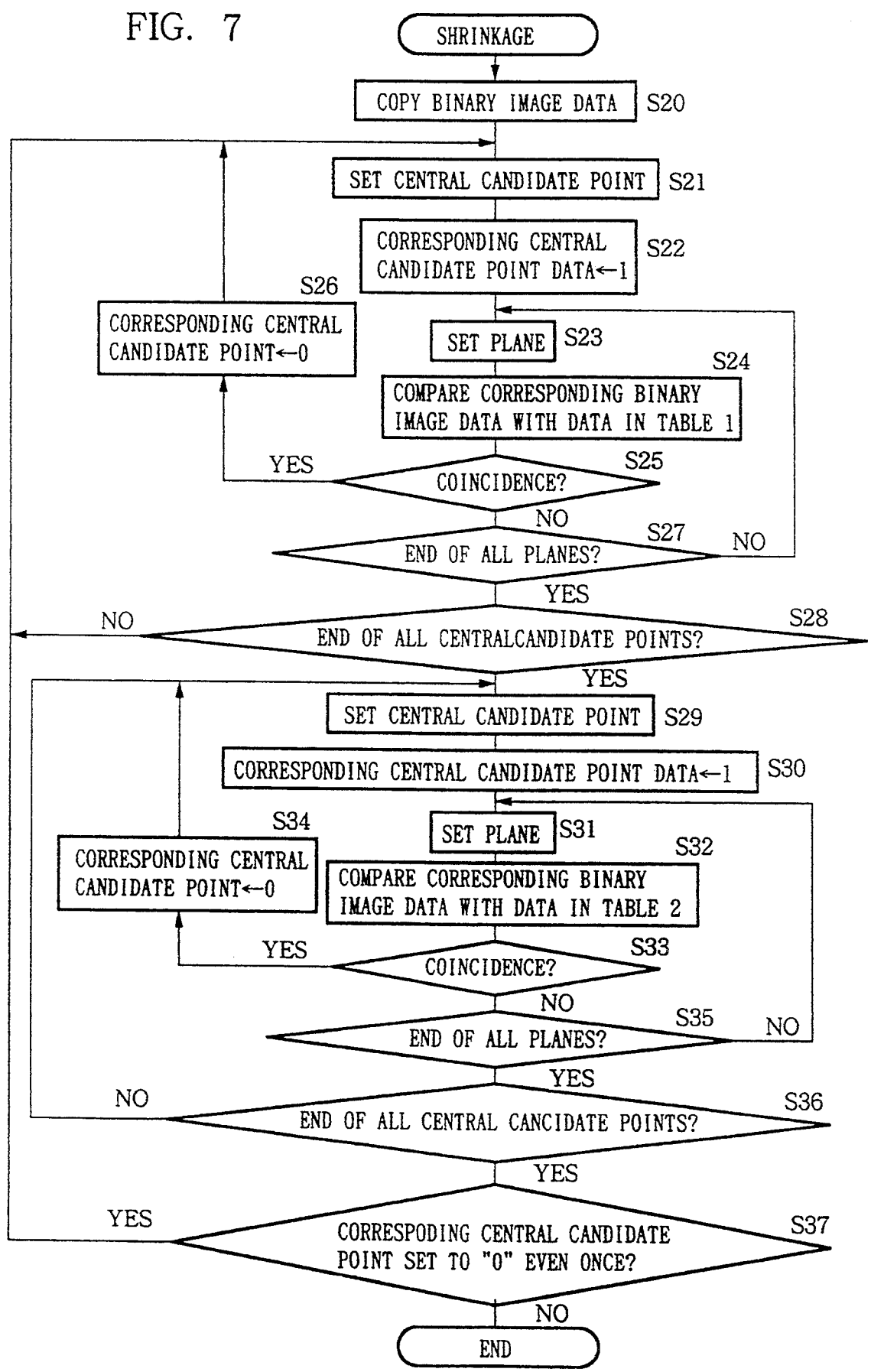
FIG. 7 is a flow chart showing shrinkage process in the apparatus of FIG. 1.

As shown in FIG. 7, to prevent destruction of the contents of binary image data to be compared with each other, binary image data are copied, and the copied data serve as corresponding data (step S20). More specifically, the results of the respective shrinkage steps are sequentially reflected on the copied corresponding binary image data. A central candidate point to be processed first is then set (step S21), and the first plane (Z plane) including this point is set (step S23). A total of nine points, i.e., the central candidate point included in this plane and eight points adjacent to the central candidate point, are compared with each data set of nine points in Table 1 while the positional relationship remains the same (step S24). It is determined in step S25 whether a case wherein all the corresponding points coincide with each other (excluding * as described above) exists. If YES in step S25, the density of the corresponding central candidate point data is set to "0" (step S26), and the flow returns to step S21 to set the next central candidate point and repeat the above operations. However, if NO in step S25, the density of the corresponding central candidate point data is set to "1" (step S22), and the flow advances to step S27.

It is determined in step S27 whether processing of all the planes is completed. If NO in step S27, the flow returns to step S23 to set the next plane and repeat the same operations as described above. However, if YES in step S27, the flow advances to step S28. It is determined in step S28 whether processing of all the central candidate points is completed. If NO in step S28, the flow returns to step S21 to set the next central candidate point. However, if YES in step S28, the flow advances to step S29 to repeat the same operations as above operations in steps S21 to S28 using the data in Table 2 (steps S29 to S36).

When filtering of all the central candidate points using Tables 1 and 2 is completed, it is determined whether the corresponding central candidate point becomes "0" even once (step S37). If YES in step S37, the flow returns to step S21 to repeat the same operations as described above. However, if NO in step S37, processing is ended. Therefore, the corresponding binary image data becomes binary data representing only the center of the particle, as indicated by the pixel 27 in FIG. 2.

The coordinates of the central position of each particle can be accurately obtained from the shrinked binary image data which confirms the center of the particle as described above. The number of particles contained in a predetermined region can be counted on the basis of the shrinked binary image data. Therefore, the density of particles and the density distribution in the predetermined region can also be detected.

The size of the particle can also be detected on the basis of the density of the gray image data of the tomographic image group at the particle position represented by the shrinked binary image data because the image density of the center of the particle has a predetermined relationship with the radius of this particle.

As shown in FIG. 8, the shrinked binary image data and the gray image data of the original tomographic image group can also be used to easily reconstruct the gray image data of the tomographic image group in a desired coordinate system L-M-N because the coordinates of the central point of each particle are accurately known.

The gray image data of the tomographic image group of the sample can be obtained by X-ray topography, X-ray CT, MRI (Magnetic Resonance Imaging) or the like in addition to the above-mentioned light scattering method.

The particle defined in the present invention may be a void, a foreign substance, or the like in addition to the precipitate, which allows formation of a particle-like image.

Figure 9A:
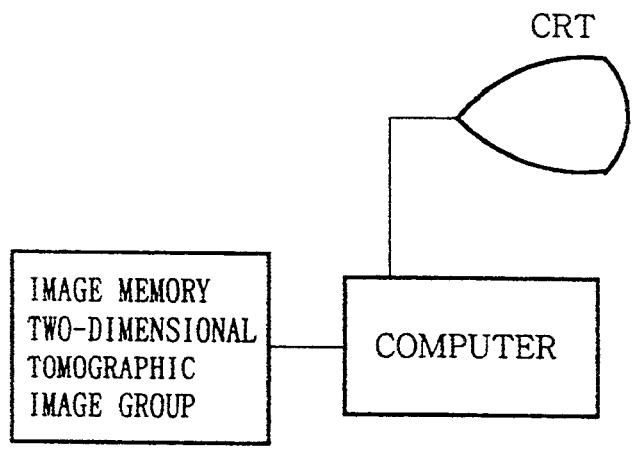
FIGS. 9a and 9b are block diagrams showing other arrangements of the apparatus according to the present invention.
Figure 9B:
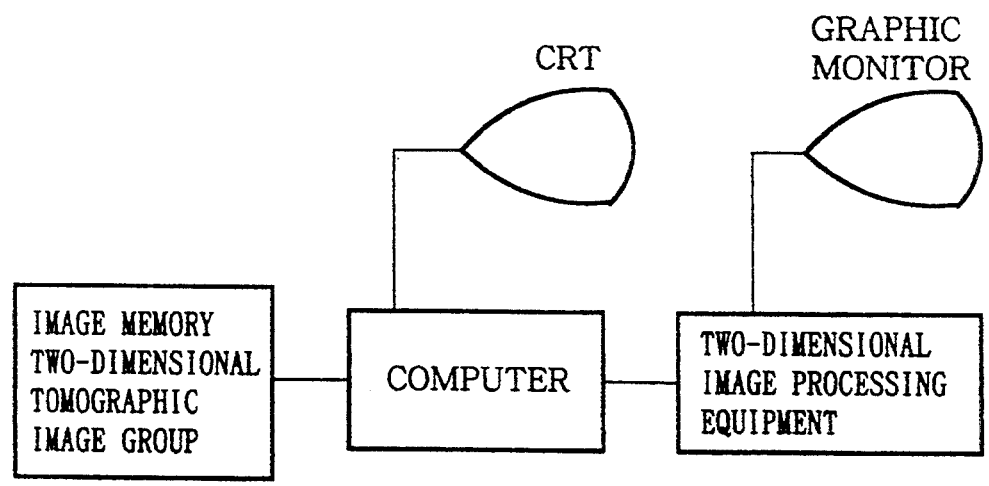
Figure 10B:
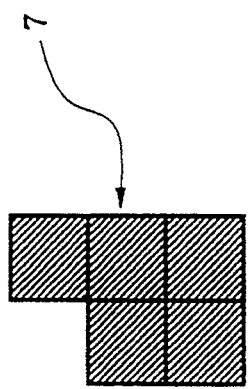
FIG. 10 is a view for explaining a conventional method of analyzing a particle.
Figure 10C:
Figure 10A:
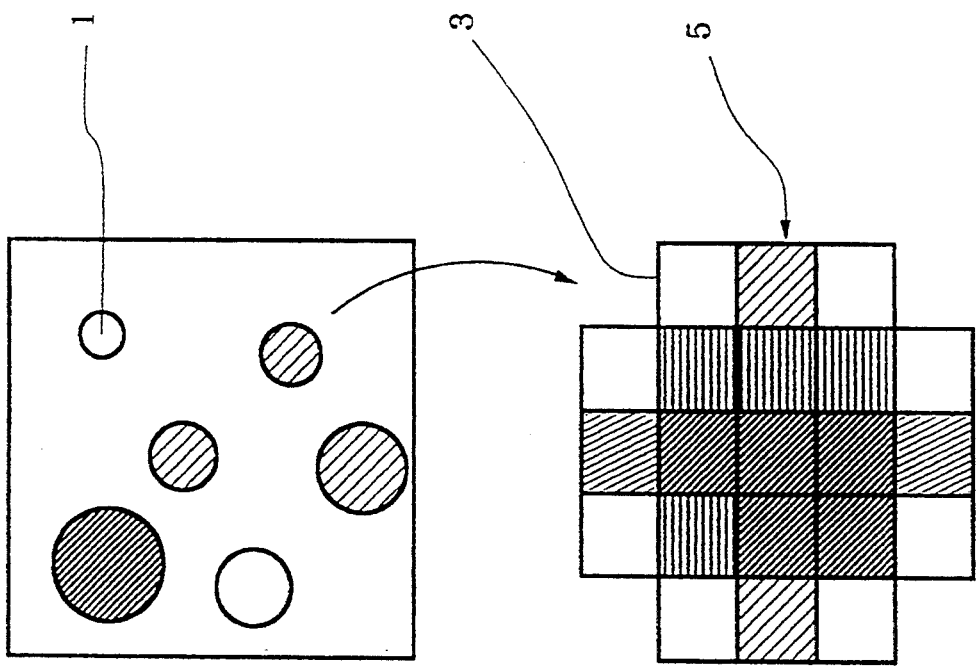
Figure 11:
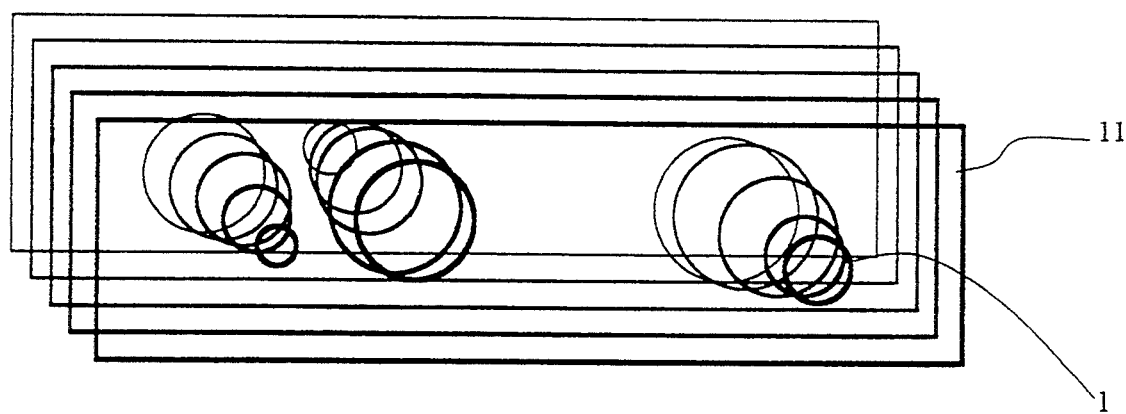
FIG. 11 is a view for explaining a two-dimensional tomographic image group in this conventional method.

A special image processing equipment, a two-dimensional image processing equipment shown in FIG. 9b, or a three-dimensional image processing equipment constituted by a general computer as shown in FIG. 9b a may be used in place of the three-dimensional image processing equipment 18. That is, processing performed in the three-dimensional image processing equipment 18 can also be performed by a two-dimensional image processing apparatus if the arrangement of data is changed.

The three-dimensional image processing equipment 18 may have an input function, and data may be directly loaded from the image memory 15. Alternatively, data may be directly input from a TV camera or image output apparatus to the three-dimensional image processing equipment 18. That is, the three-dimensional image processing equipment may be arranged to directly process data of a two-dimensional tomographic picture group.

The binarization and shrinkage methods are not limited to specific ones, but various modified methods may be proposed. Shrinkage is not limited to the method using the Rao algorithm if the data can be three-dimensionally binarized and shrinked.

If a liquid or gas is used as a sample, a pulsed laser beam can be diverged by a cylindrical lens and converged by a spherical lens to obtain a plate-like beam. This beam can be incident in a cell containing the liquid or gas, and light scattered from the cell can be photoelectrically converted by a two-dimensional image pickup element to obtain gray image data of a tomographic image group. In this case, the pulse width (time) is set such that the product of pulse width and the maximum speed ($v_{max}$) of the particle is much smaller than the measured spatial resolution. In this case, data may be acquired at each moment corresponding to each slice while the incident position of the laser beam is being moved in a direction perpendicular to the plate-like beam, thereby obtaining a tomographic image at high speed. Note that $v_{max} \cdot \tau$ (where v is the particle speed and $\tau$ is the pulse width of the pulsed laser beam) is set to be smaller than the spatial resolution of the measurement system. For example, if $v_{max}$ is 10 mm/sec, i.e., 104 μsec, then $\tau = 10^{-4}$ to $19^{-5}$ sec can be set.

If a three-dimensional image processing equipment using a computer capable of directly calculating three-dimensional data can be arranged, the Rao shrinkage performed using Tables 1 and 2 can be performed using a 3×3×3 stereoscopic filter without using a two-dimensional filter, thereby processing the data at high speed.

In addition, the two-dimensional tomographic image group serving as a target object according to the present invention also includes a tomographic image group captured as a change in time on the same slice. For example, if a precipitated particle is produced and then disappears, the time axis is added to the two dimensions to obtain an image every predetermined period of time on a given slice, thereby constructing a three-dimensional image. On the basis of this three-dimensional image, the generation position, generation time, peak value of the particle, and the like can be detected.

According to the present invention, even if a plurality of particles overlap each other in a direction perpendicular to a slice or a plurality of particles are present within a laser beam diameter, these particles can be individually decomposed, and the position, size, and structure of each particle can be accurately detected because the gray image data of the tomographic image group is subjected to binarization and three-dimensional shrinkage.

The present invention can be effectively used to determine the growth condition of a crystal required to obtain necessary physical properties and a subsequent heat-treatment condition. For example, in observation of a defect in a crystal, the method of the present invention can accurately evaluate the defects when an epitaxial layer is formed on the crystal surface, and defects near the surface in a depth of several μm from the surface are regarded as decisive defects in a semiconductor device. That is, as shown in FIG. 8, the distributions of three-dimensionally distributed defects can be known in units of layers.

What is claimed is:

1. A method of three-dimensional detection of particles, comprising the steps of: obtaining gray image data of a tomographic image group having a clear positional correlation in a sample where particles are distributed, thereby obtaining three-dimensional gray image data of each particle; performing binarization of a density of each pixel data of the three-dimensional gray image data to obtain three-dimensional binary image data of each particle; and performing three-dimensional shrinkage of the three-dimensional binary image data to convert binary image data of each particle to binary image data of only a central point thereof, thereby three-dimensionally confirming a position of each particle.

2. A method according to claim 1, further comprising the step of counting the number of particles contained in a predetermined region to detect a density of the particles on the basis of the shrinked binary image data.

3. A method according to claim 1, further comprising the step of detecting a size of a particle at a particle position represented by the shrinked binary image data, on the basis of the gray image data of the tomographic image group.

4. A method according to claim 1, further comprising the step of reconstructing gray image data of a tomographic image group in a desired direction on the basis of the shrinked binary image data and the gray image data of the tomographic image group.

5. A method according to claim 1, wherein said sample is a semiconductor crystal, and the tomographic image group is obtained such that a laser beam is radiated into said semiconductor crystal and light scattered by the particles in said semiconductor crystal is photoelectrically converted.

6. A method according to claim 1, wherein said sample is a fluid, and the tomographic image group is obtained such that a plate-like laser beam obtained using a cylindrical lens is radiated into said fluid within a short period of time, and light scattered by the particles in said fluid is photoelectrically converted, the short period of time being a time interval defined such that a product of a pulse width of the laser beam and a maximum speed of the particles contained in said fluid is set small enough to obtain a desired resolution in detection of the particles.

7. A method according to claim 1, wherein the three-dimensional gray image data is constituted by a plurality of tomographic images obtained every predetermine period of time at a predetermined slice position of said sample and has a time axis as the third dimension.

8. A method according to claim 1, wherein the step of performing binarization comprises the step of comparing the density of each pixel data of the gray image data constituting an image of the particle with densities of 26 pixel data adjacent to said each pixel data.

9. A method according to claim 1, wherein the step of performing three-dimensional shrinkage comprises the step of three-dimensionally applying a two-dimensional Rao algorithm.

10. An apparatus for three-dimensional detection of particles, comprising: gray image data forming means for obtaining gray image data of a tomographic image group having a clear positional correlation in a sample where particles are distributed, thereby obtaining three-dimensional gray image data of each particle; binary image data forming means for comparing a density of each pixel data of the three-dimensional gray image data with a predetermined value to perform binarization, thereby obtaining three-dimensional binary image data of each particle; and confirming means for performing three-dimensional shrinkage of the three-dimensional binary image data to convert binary image data of each particle into binary image data of only a central point thereof, thereby three-dimensionally confirming a position of each particle.

11. An apparatus according to claim 10, wherein said gray image data forming means comprises means for illuminating each slice and means for photoelectrically converting light scattered by said slice.

12. An apparatus according to claim 10, wherein said sample is a fluid, and said gray image data forming means obtains the tomographic image group such that a plate-like laser beam obtained using a cylindrical lens is radiated into said fluid within a short period of time, and light scattered by the particles in said fluid is photoelectrically converted, the short period of time being a time interval defined such that a product of a pulse width of the laser beam and a maximum speed of the particles contained in said fluid is set small enough to obtain a desired resolution in detection of the particles.

13. An apparatus according to claim 10, wherein said gray image data forming means forms the three-dimensional gray image data by a plurality of tomographic images obtained every predetermine period of time at a predetermined slice position of said sample and defines a time axis as the third dimension.

14. A method according to claim 10, wherein said binary image data forming means performs the binarization by comparing the density of each pixel data of the gray image data constituting an image of the particle with densities of 26 pixel data adjacent to said each pixel data.

15. An apparatus according to claim 10, wherein said confirming means performs the three-dimensional shrinkage by three-dimensionally applying a two-dimensional Rao algorithm.

* * * * *